United States Patent

Sharma et al.

[11] 4,018,822
[45] Apr. 19, 1977

[54] THIOAMINOPHOSPHAZENES

[75] Inventors: Vijay Ratna Sharma; John Anthony Taylor, both of Manchester, England

[73] Assignee: Imperial Chemical Industries Limited, London, England

[22] Filed: July 29, 1975

[21] Appl. No.: 600,190

[30] Foreign Application Priority Data

Sept. 9, 1974 United Kingdom ............ 39264/74

[52] U.S. Cl. .................... 260/551 P; 260/79.5 PR; 260/927 N; 260/940; 260/959; 260/551 S; 260/556 A; 260/556 AR
[51] Int. Cl.[2] ..................... C07F 9/22; C07F 9/23; C07F 9/24
[58] Field of Search ........ 260/551 P, 551 S, 927 N, 260/959

[56] References Cited
UNITED STATES PATENTS 3,932,403  1/1976  Ashton et al. ............ 260/551 P X
3,933,907  1/1976  Ashton et al. ............... 260/551 P

*Primary Examiner*—Daniel E. Wyman
*Assistant Examiner*—Thomas A. Waltz
*Attorney, Agent, or Firm*—Cushman, Darby & Cushman

[57] ABSTRACT

Thioaminophosphazenes containing at least one group of the formula:

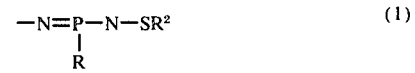

in which R is H, optionally substituted monovalent hydrocarbyl or optionally substituted divalent hydrocarbyl joining together two nitrogen atoms, $R^2$ is optionally substituted hydrocarbyl, and represented by the formula:

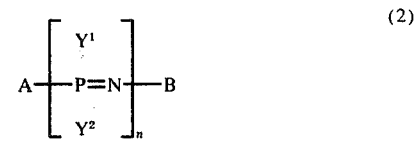

wherein $n = 1$ to 100, $Y^1$ and $Y^2$ together represent O or S, or each independently represents a monovalent substituent selected from Cl, Br, optionally substituted hydrocarbyl, optionally substituted hydrocarbyloxy and

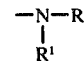

where R has the above meaning and $R^1$ is H, optionally substituted hydrocarbyl or $-SR^2$, A is a monovalent substituent of the class defined for $Y^1$, B is H, $R^2$, $SR^2$, $COR^2$ or $SO_2R^2$, or if n is 3 or more, A and B together may represent a direct link between $-P=N-$ units in a cyclic structure.

The products are useful in preventing premature vulcanization in vulcanizable rubber compositions.

6 Claims, No Drawings

THIOAMINOPHOSPHAZENES

This invention relates to thioaminophosphazenes of value as inhibitors of premature vulcanisation in rubbers.

It is customary in the manufacture of vulcanised rubbers to incorporate into the unvulcanised rubber various additives such as antioxidants, antiozonants, fillers, vulcanisation activators, etc., and lastly vulcanisation accelerators and a vulcanising agent such as sulphur. The compounded rubber is then shaped and finally raised to vulcanisation temperature. Before the final stage, however, some premature vulcanisation may take place, especially during the compounding stage in a mill or Banbury mixer when heat is generated, or during handling such as calendering or extruding, or in some cases even during storage. Premature vulcanisation causes the rubber to become lumpy with the result that subsequent processing or vulcanising operations cannot be carried out satisfactorily. Premature vulcanisation may be reduced by using delayed action accelerators of for example the benzthiazyl sulphenamide type and also by the use of retarders such as N-nitrosodiphenylamine or salicyclic acid but these retarders frequently introduce other difficulties. No satisfactory means of preventing premature vulcanisation has hitherto been found and the increasing use of furnace carbon blacks and of antioxidants and antiozonants based on p-phenylenediamine has exacerbated the problem. It has now been found that certain novel thioaminophosphazenes are powerful inhibitors of premature vulcanisation.

According to the invention there are provided, thioaminophosphazenes having at least one group of the formula:

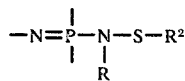
(1)

where R is H, optionally substituted monovalent hydrocarbyl or optionally substituted divalent hydrocarbyl joining together two nitrogen atoms and $R^2$ is optionally substituted hydrocarbyl.

In particular there are provided thioaminophosphazenes of the above type represented by the formula:

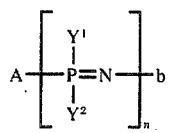
(2)

wherein
$n = 1 - 100$, $Y^1$ and $Y^2$ together represent O or S, or each independently represents a monovalent substituent selected from Cl, Br, optionally substituted hydrocarbyl, optionally substituted hydrocarbyloxy and

where $R^1$ is H, optionally substituted hydrocarbyl or $-SR^2$, and R and $R^1$ have the meanings given above, A is a monovalent substituent of the class defined for $Y^1$, B is H, $R^2$, $SR^2$, $COR^2$ or $SO_2R^2$, or if $n$ is 3 or more, A and B together may represent a direct link between $-P=N-$ units in a cyclic structure.

The above definition provides for compounds containing two or more groups which may be designated by the same symbols, for example $Y^1$, $Y^2$ $R-N-R^1$, $S-R^2$ and it is intended that the meanings given to R, $R^1$ and $R^2$ may be the same or different for each such grouping.

As examples of the groups represented by A, $Y^1$ and $Y^2$ there may be mentioned hydrocarbyl groups especially $C_{1-25}$ groups such as alkyl, for example methyl, ethyl, isopropyl, sec butyl and n-dodecyl, alkenyl, for example propenyl, but-1-en-4-yl, octenyl and hexadecenyl, cycloalkyl, for example, cyclopentyl and cyclohexyl, aryl, for phenyl, o-, m- and p-tolyl and naphthyl, aralkyl, for example benzyl, phenylpropyl and phenylethyl, substituted hydrocarbyl groups such as methoxymethyl, alkyloxycarbonyl, β-cyanoethyl, 2-formylprop-2-yl, 4-chlorophenyl, 4-methoxyphenyl, 4-dimethylaminophenyl, 2-nitrophenyl, 4-nitrophenyl, 2,3,4,5, 6-pentachlorophenyl, 2-methoxycarbonylphenyl, 4-phenyl-sulphonylphenyl, hydrocarbyloxy groups such as methoxy, ethoxy, isopropoxy, butoxy, hexyloxy, octyloxy, phenoxy, cresyl, xylyloxy or substituted hydrocarbyloxy groups such as β-methoxyethoxy, β-cyanoethoxy, β-chloroethoxy, o- or p-cholophenoxy, o-or-p-methoxy phenoxy.

As examples of the optionally substituted hydrocarbyl group represented by $R^2$ or R when a monovalent group there may be mentioned the groups given above as examples hydrocarbyl and optionally substituted hydrocarbyl groups.

As examples of optionally substituted divalent hydrocarbyl groups represented by R there may be mentioned optionally substituted alkylene groups which may or may not be interrupted by heteroatoms such as butylene, hexylene $CH_2CH_2-O-CH_2CH_2$, $CH_2CH_2-S-CH_2CH_2$ or substituted alkylene groups such as 2-methylbutylene, 2-chlorobutylene $CH_2.CHCL.CH_2.O.CH_2CHCl.CH_2$, or arylene groups such as 1,3- and 1,4-phenylene, or substituted arylene groups such as 2-chloro-1,4-phenylene, 2-nitro-1,4-phenylene.

Any of the optionally substituted divalent hydrocarbyl groups described above may link nitrogen atoms attached to different

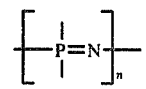

systems or link together two nitrogen atoms attached to the same or different phosphorus atoms of the same

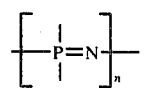

system, thus forming a heterocyclic ring incorporating any intervening phosphorus and nitrogen atoms. The suitability of any grouping in forming the heterocyclic rings mentioned above is naturally subject to the usual consideration of their being able to form appropriate steric configurations. For such steric considerations arylene groups are much less likely to be suitable for forming the heterocyclic ring although some such groups e.g. 1,2- phenylene groups can form ring structures in certain cases.

The symbol n in formula (2) may be any number between 1 to 100. For example, n may be from 1 to 5. Compounds in which $n\not=1$ are a preferred class. In the case of linear polymers of P=N units it is preferred that n is from 2 to 20 especially from 2 to 5. With cyclic polymers of P=N units it is preferred that n is from 3 to 5 and a value of 3 is particularly preferred.

A preferred class of compounds as defined above by formula (2) are monocyclic thioaminophosphazenes of the formula:

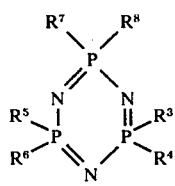
(3)

wherein $R^3$, $R^4$, $R^5$, $R^6$, $R^7$ and $R^8$ each have the meaning stated above for the symbol A, especially R—N—$R^1$ and at least one is a R–N–S–$R^2$ group, wherein R, $R^3,R^4,R^5,R^6,R^7$ and $R^8$ are free from radicals linking two phosphorus atoms.

A further preferred class of compounds as defined above by formula (2) are those in which the group A, if present, $Y^1$ and $Y^2$ are all of the formula R—N—$R^1$ where R and $R^1$ have in each case any of the meanings stated above and at least one is a R—N—S—$R^2$ group.

An especially preferred class of compound as defined above by formula (2) are those of formula (3) wherein $R^3,R^4,R^5,R^6,R^7$ and $R^8$ all represent R-N-S-$R^2$ where R and $R^2$ have the meanings given in connection with formula (2).

As examples of thioaminophosphazenes of the present invention there may be mentioned, P,P,P-tris[N-(methylthio)anilino]-N-benzene sulphonyl phosphine imide, P,P,P-tris[N-(isopropylthio)anilino]-N-phenyl phosphine imide, P,P,P′,P′,P″,P″-hexakis[N-(isopropylthio)anilino]cyclotriphosphazene,P,P,P′,P′,P″,-P″-hexakis[N-(methylthio)p-toluidino]cyclotriphosphazene, P,P,P-tris[N-(phenylthio)methylamino] phosphine imide P,P,P-tris[N-n(butylthio)p-methoxyphenylamino]phosphine imide P,P,P-tris[N-(phenylthio)cyclohexylamino] phosphine imide, (P,P-diphenyl-P-[N-(cyclohexylthio)phenylamino]phosphine imide, P,P,P′,P′,P″,P″-hexakis [N-(trichloromethylthio)phenylamino] cyclotriphosphazene and P,P,P′,P′, P″,P″,P‴,P‴-octakis[N-(methylthio)phenylamino]-cyclo tetraphosphazene.

P,P,P′,P′,P″,P‴ hexakis methoxy -P″, P‴-di[N-(ethylthio) cyclohexylamino] cyclotetraphosphazene, P,P,P′,P′,P″,P″,P‴,P‴octakis[N-(phenylthio)-β-cyanoethylamino]cyclotetra phosphazene, P,P,P,P′,P′-[N-(isobutylthio)anilino]-N-p-toluene sulphonyl diphosphazene P,P,P′,P′-tetrakis ethoxy -P-[N-(isopropyl thio)-p-methoxyl phenyl amino]-N-methane sulphonyl diphosphazene, P,P,P′,P′,P″,P″-hexakis isopropoxy-P-[N-(secbutylthio)cyclohexylamino]-N-l-naphthalene sulphonyl triphosphazene, P,P,P′,P′,P″,P″,P‴,P‴-octakis-n-butoxy-P-[N-(p-methoxyphenyl thio)anilino]N-formyl tetraphosphazene, P,P,P′,P′,P″,P″,P‴,P‴,P″″,P″″-decakis phenoxy-P-[N-(methylthio)methyl amino]N-benzene sulphonyl pentaphosphazene, P,P′,P″-triscresyl-P,P′,P″-tris[N-isopropylthio)p-toluidino]-cyclotriphosphazene, P,P′-dixylyloxy-P,P,P′-tris[N-(methylthio)cyclohexylamino]-N-methane sulphonyl diphosphazene, P,P-di-p-chlorophenoxy-P-[N-(isopropylthio)anilino]-N-p-toluenesulphonyl phosphazene, P,P-diethoxy-P-[N-(methylthio)anilino]-N-acetyl phosphazene, 2-[N-methylthio)methylamino]-2-[N-methanesulphonylimino]-4:5 benzo -1:3 diaza-2-phospholane, P,P-dihexyloxy-P-[N-(ethylthio)cyclohexylamino]-N-benzoylphosphazene, P,P,P′,P″-tetrakis hexyloxy-P′,P″-di-[N-(ethylthio)-o-toluidino]-cyclo triphenazene, P,P′,P″-trismethoxy-P,P′,P′-tris[-N-(isopropylthio)anilino]-cyclotriphenazene, P-anilino-P-dimethylamino-P-[N-(isopropylthio)anilino]-N-benzoyl phosphazene, P-butoxy-P-di-β-cyanoethylamino-P[-N-(secbutylthio)methylamino]-N-benzene -sulphonyl phosphazene.

By way of explanation it may be noted that various forms of nomenclature exist for compounds of the above types in which the P=N entity may have various essentially equivalent designations e.g. phosphine imide,phosphazene and phosphine imine.

The invention further provides a process for the manufacture of the thioamino-phosphazenes of the present invention which comprises reacting aminophosphazenes having at least one

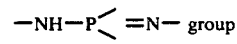

with a sulphenyl halide of the formula $R^2$—S—Y where Y = Cl or Br and $R^2$ has the meaning given above. This reaction is normally conducted in reaction media such as carbon tetrachloride, toluene, cyclohexane or ethyl acetate at temperatures of —20° to 120° C preferably from 30° to 80° C.

Amounts of $R^2$—S—Y employed normally range from 0.1 to 1.0 moles per mole of NH group in the aminophosphazene. The final products normally have from 0.8 to 1.0 especially 1.0 $R^2$—S—N for every NH group originally present in the aminophosphazene.

The ammophosphazenes having NH groups used in the above process may be obtained by conventional means such as reacting phosphonitrilic halides of the formula

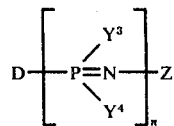

where n is 1 to 100, at least one of D, $Y^3$ and $Y^4$ is Cl or Br, and the remainder are Cl, Br or optionally substituted hydrocarbyl and Z is H or R², R²CO or R²SO₂ or when n is 3 or more D and Z together may be a direct link between

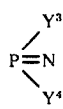

units in a cyclic structure, with R²NH₂ and optionally (R²)₂ NH and/or R²OH where R² has the meaning given above.

The phosphonitrilic halides of the formula

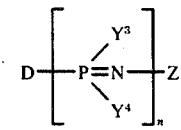

mentioned above are obtained by known methods, for example, by the interaction of phosphorus halides such as diphenyl trichloro-phosphorane and especially phosphorus pentachloride or pentabromide with ammonia, ammonium halides, amines of the formula R² — NH₂ or their hydrohalides, amides of the formula R²—CONH₂ or sulphonamides of the formula R².SO₂.NH₂ where R² has the meanings given above. This conveniently takes place at −50° to 150° C in reaction media such as toluene, carbon tetrachloride or cyclohexane.

The phosphonitrilic halides may be reacted with amine R²NH₂ and optionally (R²)₂NH and/or R²OH at −20 to 250° C preferably at from 50° to 120° C in reaction media such as excess amine, cyclohexane, carbon tetrachloride, toluene or tetrahydrofuran.

The amount of amine (R²)₂NH and R²NH₂ and hydroxy compound R²OH used in this reaction will normally be sufficient to react with all the halogen atoms present in the phosphonitrilic halide and an excess of amine may be used to ensure complete reaction. However in some circumstances it may be desirable to use a deficiency of amine to leave a proportion of halogen atom on the phosphorus, possibly for reaction with other compounds.

The intermediate reaction product of the phosphonitrilic halide and R²NH₂ and optionally (R²)₂NH and/or R²OH may be reacted, with or without any preliminary isolation or purification steps with compounds of the formula R² — S — Y.

The final product may be subjected to any conventional isolation or purification procedures such as washing, extraction or distillation.

As examples of phosphonitrilic halides which may be used to obtain starting materials for use in the process of the present invention there may be mentioned:

Hexachlorocyclotriphosphazene, octachlorocyclotetra phosphines, linear polymers derived from phosphorus pentachloride and ammonium chloride, P,P,P-trichloro-N-benzenesulphonyl phosphine imide and P,P,P,-trichloro-N-phenylphosphine imide.

As examples of the amines (R²)₂NH there may be mentioned dimethylamine, diethylamine, dicyclohexylamine, N-methylaniline and dicyclohexylamine and as examples of R²NH₂ there may be mentioned methylamine, ethylamine, iso-propylamine, aniline, cyclohexylamine, p-anisidine and o-toluidine.

As examples of R²OH there may be mentioned methanol, ethanol, isopropanol, butanol, hexanol, octanol, phenol, o,m and p-cresol, xylenols, o- and p- chlorophenol, o- and p- methoxyphenol.

If it is desired to produce thioaminophosphazenes of formula (2) containing a group

wherein R is an optionally substituted divalent hydrocarbyl radical joining together two nitrogen atoms, the process of the present invention should employ an appropriate amino-phosphazene obtained from a phosphonitrilic halide reacted with a diamine and optionally R²NH₂, (R²)₂NH or R²OH providing that some reactant or reactants contains groups which will provide NH in the aminophosphazene. As examples of such diamines there may be mentioned ethylene diamine, hexamethylene diamine, butylene diamine, H₂NCH₂CH₂OCH₂CH₂NH₂, H₂NCH₂CH₂SCH₂CH₂NH₂ 2-methyl butylene diamine, 1,2-, 1,3- or 1,4 phenylene diamine, 2-chloro-1,4-phenylene diamine and 2—nitro-1,4-phenylene diamine.

As examples of the sulphenyl halides R²—S—Y for use in the process of the present invention there may be mentioned methane sulphenyl chloride, ethane sulphenylchloride, isopropylsulphenyl chloride, sec butylsulphenylchloride, trichloromethylsulphenyl chloride, cyclohexylsulphenyl chloride, methane sulphenyl bromide, phenylsulphenyl chloride, p-methoxy phenylsulphenyl chloride, 2-formylprop-2-sulphenyl chloride β-naphthylsulphenyl chloride and 4-tertbutylphenyl sulphenyl chloride.

According to the invention there is further provided a process for reducing the premature vulcanisation in a rubber containing a vulcanising agent and a vulcanisation accelerator which comprises incorporating in the rubber a thioaminophosphazene as hereinbefore defined.

The vulcanising agent used in this second process of the invention may be a sulphur donor, such as N,N'-dithiobismorpholine, N,N'-dithiobis-caprolactam, tetramethylthiuram disulphide, diethylthiophosphoryl disulphide or diethylthiophosphenyl trisulphide or preferably elemental sulphur, or for example a peroxide or other type of vulcanising agent.

The vulcanisation accelerator used in the second process of the invention is preferably a sulphenamide such as N-cyclohexyl-benzothiazole-2-sulphenamide, N-t-butylbenzothiazole-2-sulphenamide, N-diethyleneoxybenzothiazole-2-sulphenamide or N-dicyclohexylbenzothiazole-2-sulphenamide, a thiazole such as mercaptothiazole, 2-mercaptobenzothiazole or its metal salts, e.g. zinc, sodium or copper salt or dibenzothiazyl disulphide or a thiuram such as tetramethylthiuram monosulphide, tetramethylthiuram disulphide, tetramethylthiuram tetrasulphide, tetraethylthiuram monosulphide, tetraethylthiuram disulphide, or a metal salt of a dithiocarbamate such as zinc dimethyldethiocarbamate or sodium diethyldithiocarbamate.

Other types of accelerator may however be used such as diaryl guanidines, thioureas, xanthates or aldehydeamine condensates, or mixtures of any of these and the above accelerators.

The amounts of vulcanisation agent and accelerator may be those conventionally used in the manufacture of rubber vulcanisates.

The amount of thioaminophosphazene may be from 0.01% to 5% and preferably from 0.05 to 2.5% of the weight of the rubber.

Rubbers which may be used in the second process of the invention include both natural and synthetic rubbers and mixtures thereof. The synthetic rubber may in general be any polymeric material containing olefinic unsaturation and capable of being crosslinked by particularly sulphur, but also be peroxide or other crosslinking agents. Examples of synthetic rubbers include cis-polybutadiene, butyl rubber, ethylene-propylene terpolymer, polymers of 1,3-butadienes such as isoprene and chloroprene and copolymers of 1,3-butadiene with other monomers such as styrene, acrylonitrile and isobutylene.

The thioaminophosphazene may be incorporated into the rubber by any conventional dry rubber or latex compounding procedure, for example on a rubber mill, in an internal mixer, through a screw type extruder blender, as a solution in an organic solvent or as an aqueous dispersion. If desired the latex into which the thioaminophosphazene has been incorporated may be coagulated and converted into dry raw rubber by conventional techniques and used subsequently for making vulcanisable compositions.

According to the invention there are also provided unvulcanised rubber compositions containing a thioaminophosphazene as hereinbefore defined.

The rubber mix may also contain conventional rubber adjuvants such as antioxidants, antiozonants, fillers, peptising agents, pigments, blowing agents, and accelerator activators such as zinc oxide and stearic acid, or such adjuvants may be incorporated subsequently into the unvulcanised composition.

The invention is of particular value when the rubber composition is reinforced with a furnace black or contains a p-phenylene diamine based antiozonant since such rubber compositions are especially prone to premature vulcanisation.

Incorporation of the thioaminophosphazene into the rubber may be assisted if the thioaminophosphazene is blended with an inert inorganic diluent such as silica, alumina, calcium carbonate or Fuller's earth. Such blends, which will preferably contain from 10 to 70% of the thio aminophosphazene, represent another feature of the invention.

By the second process of the invention there are obtained vulcanisable rubber compositions which can be handled on conventional rubber processing machines or stored for long periods with little tendency to premature vulcanisation but which will cure readily at conventional vulcanisation temperatures to give vulcanisates of excellent physical properties. These vulcanisable rubber compositions, their vulcanisation by heating to conventional vulcanisation temperatures, and the vulcanisates so obtained are further features of this invention.

The invention is illustrated by the following examples in which all parts are by weight unless otherwise stated.

EXAMPLE 1

A solution of 22.6 parts of cyclohexasulphenyl chloride in 75 parts of cyclohexane is added at 30°–35° C to a well stirred mixture of hexakis (phenylamino) cyclotriphosphazene (17.2 parts) and triethylamine (15 parts) in 100 parts of cyclohexane. When the addition is complete the mixture is heated to 70° C for 30 minutes, filtered and the filtrate evaporated under reduced pressure to give a viscous red oil which on standing deposited a pale yellow solid, softening at 100°–110° C. N.m.r. and i.r. spectroscopy indicated that the product is predominantly P,P,P,'P',P'',P''-hexakis[N-(cyclohexylthio) phenylamino]cyclotriphosphazene. Found C,62.0; H,7.0; P,7.2% $C_{72}H_{96}N_9P_3S_6$ required C,62.9; H,7.05; P6.8%

EXAMPLE 2

By the same method as that of example 1, but using 16.6 parts of isopropyl sulphenyl chloride in place of cyclohexyl sulphenyl chloride, a yellow solid, softening at 80° C, is obtained which is mainly P,P,P,P',P', P'',-P''-hexakis [N-(isopropylthio)phenylamino]cyclotriphosphazene.

EXAMPLE 3

|  | Parts |
|---|---|
| Natural Rubber (SMR-5) | 100 |
| Zinc Oxide | 3.5 |
| Stearic acid | 3 |
| High Abrasion Furnace Black | 45 |
| Process Oil | 3.5 |
| Sulphur | 2.5 |
| N-Cyclohexyl-2-benzthiazyl sulphenamide | 0.5 |
| Retarder | see below |

The above ingredients are mixed on a two-roll laboratory rubber mill in conventional manner and sheeted out. Samples are cut and tested for scorch safety in a Mooney rotating disc plastometer at 120° C, and for cure characteristics in an oscillating disc rheometer at 150° C.

The results are tabulated below:

| Retarder | Mooney Scorch Minutes to reach Minimum + 10 | Rheometer Cure data | | |
|---|---|---|---|---|
| | | Induction time $T_2$ (Minutes) | Torque Peak Value (Inch lbs) | Time to reach 90% Peak torque (mins) |
| Nil | 19 | 5.8 | 69.5 | 15.5 |
| 0.25 p.h.r. of the product of Example 1. | 30 | 7.5 | 69.0 | 18.1 |
| 0.25 p.h.r. of the product of Example 2. | 37 | 8.3 | 71.0 | 18.5 |

EXAMPLE 4

A solution of 16.6 of isopropylsulphenyl chloride in cyclohexane (100 parts) was added to a well stirred mixture of P,P,P-Trianilino-N-p-toluenesulphonyl phospazene (23.8 parts) and triethylamine (24 parts) in cyclohexane (100 parts). After heating for 1 hour at 80° C insolubles were removed by filtration, the filtrate was evaporated to small volune under reduced pressure and the resulting residue chromatographed over silica gel. Elution with chloroform gave P,P-dianilino-P-(N-isopropylthioanilino)-N-p-toluenesulphonyl phosphazene.(4.25 parts) as a colourless solid m.p. 165°–167°. Found C, 59.3; H, 5.7; N, 9.9; P, 5.4; S, 10.2%; $C_{28}H_{31}N_4O_2PS_2$ requires C, 61.0; H, 5.7; N, 10.2; P,5.6; S, 11.6%.

EXAMPLE 5

Using the rubber composition and procedure given in Example 3 the product of Example 4 was tested with the following result:

| Retarder | Mooney Scorch Minutes to reach Minimum + 10 | Rheometer Cure data | | |
|---|---|---|---|---|
| | | Induction time $T_2$ (Minutes) | Torque Peak Value (Inch lbs.) | Time to reach 95% Peak Torque (Minutes) |
| Nil | 24 | 5 | 72 | 18 |
| 0.25 p.h.r. of product of Example 4 | 28½ | 5.8 | 64.4 | 18 |

We claim:
1. A thioaminophosphazene of the formula

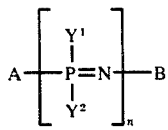

wherein $n$ is 1 to 5,
- A, if present, $Y^1$ and $Y^2$ are each selected from methoxy, ethoxy, propoxy, butoxy, hexyloxy, phenoxy, cresyl, xylyloxy, chlorophenoxy, dimethylamino, or groups of the formula —$NHR^{10}$ where $R^{10}$ is selected from phenyl, methylphenyl, methoxyphenyl, cyclohexyl, methyl or two of the groups —$NHR^{10}$ together are 1,2-phenylenediamino;
- B is selected from benzenesulphonyl, toluenesulphonyl, methane sulphonyl, naphthalene sulphonyl, formyl, acetyl or benzoyl, and
- at least one of the groups A, $Y^1$ and $Y^2$ are of the formula

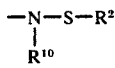

where $R^{10}$ is defined above and $R^2$ is selected from methyl, ethyl, isopropyl, isobutyl, cyclohexyl, sec-butyl, phenyl or methoxyphenyl.

2. A thioaminophosphazene as claimed in claim 1 wherein $n$ is 1.

3. A thioaminophosphazene according to claim 1 and having the formula:

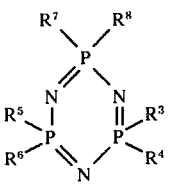

wherein $R^3$, $R^4$, $R^5$, $R^6$, $R^7$ and $R^8$ each stand for

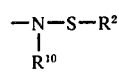

wherein $R^2$ and $R^{10}$ have the meanings given in claim 1.

4. A thioaminophosphazene as claimed in claim 3 wherein $R^3$, $R^4$, $R^5$, $R^6$, $R^7$ and $R^8$ are all

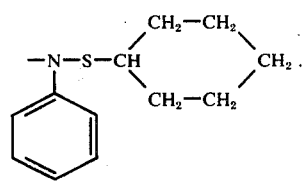

5. A thioaminophosphazene as claimed in claim 3 wherein $R^3$, $R^4$, $R^5$, $R^6$, $R^7$ and $R^8$ are all

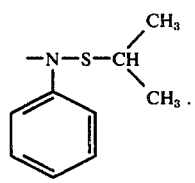

6. A thioaminophosphazene as claimed in claim 2 and having the formula

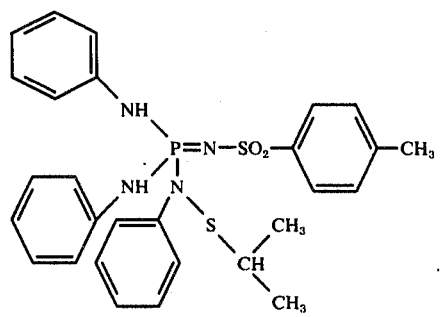

* * * * *